United States Patent [19]

Dessau

[11] Patent Number: 5,283,385
[45] Date of Patent: Feb. 1, 1994

[54] UPGRADING OF NORMAL PENTANE TO CYCLOPENTANE

[75] Inventor: Ralph M. Dessau, Edison, N.J.
[73] Assignee: Mobil Oil Corporation, Fairfax, Va.
[21] Appl. No.: 878,267
[22] Filed: May 4, 1992

Related U.S. Application Data

[60] Continuation-in-part of Ser. No. 418,377, Oct. 6, 1989, Pat. No. 5,192,728, which is a division of Ser. No. 211,198, Jun. 24, 1988, Pat. No. 4,990,710.

[51] Int. Cl.$^5$ ............................................... C07C 5/00
[52] U.S. Cl. .................................... 585/317; 585/311; 585/312; 585/313; 585/365; 585/379; 208/136; 208/137; 208/141
[58] Field of Search ............... 585/365, 313, 312, 317, 585/379; 208/136, 137, 141

[56] References Cited

U.S. PATENT DOCUMENTS

| Re. 29,948 | 3/1979 | Dwyer et al. | 208/110 |
|---|---|---|---|
| 2,387,989 | 10/1945 | Foster | 585/365 |
| 3,702,293 | 11/1972 | Hayes et al. | 208/139 |
| 3,702,294 | 11/1972 | Rausch | 208/139 |
| 3,878,131 | 4/1975 | Hayes | 252/466 PT |
| 4,104,320 | 8/1978 | Bernard et al. | 50/673.5 |
| 4,152,246 | 5/1979 | Weisang et al. | 585/482 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,485,185 | 11/1984 | Onodera et al. | 502/71 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Van Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,822,762 | 4/1989 | Ellig et al. | 502/66 |
| 4,830,729 | 5/1989 | Dessau et al. | 208/89 |
| 4,851,599 | 7/1989 | Dessau | 585/407 |
| 4,868,145 | 9/1989 | Dessau et al. | 502/66 |
| 4,882,040 | 11/1989 | Dessau et al. | 208/138 |
| 4,886,926 | 12/1989 | Dessau et al. | 585/444 |
| 4,892,645 | 1/1990 | Dessau | 208/111 |
| 4,910,357 | 3/1990 | Dessau et al. | 585/322 |
| 4,935,566 | 6/1990 | Dessau et al. | 208/65 |
| 4,990,710 | 2/1991 | Dessau et al. | 585/277 |
| 5,037,529 | 8/1991 | Dessau et al. | 208/64 |
| 5,103,066 | 4/1991 | Dessau | 568/406 |
| 5,122,489 | 6/1992 | Dessau | 502/66 |
| 5,124,497 | 6/1992 | Dessau et al. | 585/419 |

FOREIGN PATENT DOCUMENTS 2033358A  5/1980  United Kingdom.

*Primary Examiner*—Asok Pal
*Assistant Examiner*—P. Achutamurthy
*Attorney, Agent, or Firm*—Alexander J. McKillop; Dennis P. Santini; Lori F. Cuomo

[57] ABSTRACT

This invention is a process of converting n-pentane to cyclopentane. In accordance with a preferred embodiment of the invention, n-pentane feed is converted in dual temperature stage process without interstage processing of the first stage product mixture.

25 Claims, No Drawings

UPGRADING OF NORMAL PENTANE TO CYCLOPENTANE

CROSS REFERENCE TO RELATED APPLICATION

This application is a continuation in part under 35 USC 120 of copending Serial No. 418,377 filed Oct. 6, 1989, now U.S. Pat. No. 5,192,728, which, in its entirety, is incorporated by reference herein, which in turn is a division of Ser. No. 211,198 filed on Jun. 24, 1988 now U.S. Pat. No. 4,990,710.

FIELD OF THE INVENTION

The process of the invention relates to a dual stage process for conversion of n-pentane to cyclopentane. The conversion is conducted catalytically in a dual stage-dual temperature process.

BACKGROUND OF THE INVENTION

With the increase in cracking severity of FCC and the rise of hydroprocessing, the problem of processing byproduct n-pentane has become more significant. Some refineries isomerize the low 62 RON (research octane number) n-pentane to isopentane (RON=92). Isomerization of the n-pentane to isopentane leads, however, to an increase in gasoline volatility (RVP of n-pentane=15 6; RVP of isopentane=20.4); and environmental factors may limit the amount of isopentane usable in gasoline in the future.

Cyclopentane offers several advantages over both n-pentane and isopentane as a gasoline additive. Its research octane number is even higher than that of isopentane, and its volatility is substantially lower, as shown below:

| Compound | RON | MON | RVP |
|---|---|---|---|
| n-pentane | 61.7 | 62.6 | 15.6 |
| isopentane | 92.3 | 90.3 | 20.4 |
| cyclopentane | 101.3 | 84.9 | 9.9 |

Compared to pentane isomerization, cyclopentane production, in accordance with the invention, yields a higher octane product and at the same time reduces the RVP of the pentane fraction.

SUMMARY OF THE INVENTION

The process of the invention relates to catalytic conversion of n-pentane to cyclopentane in a dual temperature staged process. The catalyst in each of the two temperature stages of the process of the invention may be identical.

In accordance with the invention, the first stage product mixture is passed over the catalyst, at a lower temperature, to produce cyclopentane. In accordance with a preferred embodiment of the invention, the product mixture of the first stage is subjected to second stage temperature conditions, without interstage processing of the product mixture resulting from the first stage.

DETAILED DESCRIPTION OF THE INVENTION

Dual Stage Process Conditions

First Stage Process Conditions

The catalyst in the two stages may be the identical catalyst or not. In accordance with the invention, the first stage comprises contacting a feed comprising n-pentane, with a Group VIII metal or Group VIA metal containing non-acidic catalyst composition.

In accordance with the invention, the first stage of the catalytic process is conducted at elevated temperatures ranging from 300° C. to 700° C., and, preferably from 400° C. to 600° C., and most preferably at a temperature ranging from 450°–600° C. In the first stage, pressure conditions include pressures varying from subatmospheric, to atmospheric to greater than atmospheric. Preferred pressures range from 0.1 atmospheres to atmospheric. However, pressures up to 100 psig can be employed. The weight hourly space velocity ranges from 0.02 to 50, preferably from 0.1 to 10.

The first stage may be conducted in the presence or absence of purposefully added hydrogen and preferably, in the presence of diluents inert to conditions of the catalytic dehydrogenation such as nitrogen and methane, and aromatics including $C_6$–$C_8$ aromatics [benzene, toluene, xylene(s) including the o-, m- and p-isomers] and admixtures thereof. In particular, the first stage can be advantageously conducted in the absence of added hydrogen.

In the first stage, the feed is n-pentane and any feed containing n-pentane.

Accordingly, the second stage of the process comprises subjecting the product effluent of the first stage, to the second stage conditions.

The catalyst in the first stage may be identical to the catalyst used in the second stage and is described below. In accordance with the invention, the second stage catalysis comprises contacting a feed comprising the product effluent of the first stage with a Group VIII metal containing non-acidic microporous crystalline catalyst composition, to produce cyclopentane.

The second stage of the process is conducted at temperatures lower than the temperature in the first stage of the process. In accordance with the invention, catalytic conditions in the second stage include pressures varying from subatmospheric, to atmospheric to greater than atmospheric. Preferred pressures range from 0.1 atmospheres to atmospheric. However, pressures up to 100 psig can be employed. The second stage of the process of the invention is conducted at temperatures ranging up to less than about 300° C., typically from at least 25°–250° C.

The weight hourly space velocity will range from 0.02 to 50, preferably 0.1 to 10.

Although the product mixture effluent resulting from the first stage catalysis can be subjected to interstage processing prior to introduction to the second stage of the process, preferably the product mixture resulting from the first stage is not subjected to interstage processing prior to introduction to the second stage of the process. In a preferred embodiment, the two stages are conducted in a cascade operation. The catalytic stages of the process of the invention can be undertaken in fixed bed, moving bed and/or fluidized bed reactor.

As a result of the two stage catalysis, cyclopentane is produced.

The Catalyst

Another aspect of the invention is the catalyst comprising a Group VIA or a Group VIII metal and a non-acidic microporous material. The non-acidic microporous material can also be "crystalline" in the sense that it has a unique X-ray diffraction pattern. Preferably, the microporous crystalline material contains a modifier selected from the group consisting of tin, indium, thallium, lead, gallium and sulfur. The preferred catalysts are described in allowed U.S. patent application Ser. No. 418,377, filed Oct. 6, 1989, and its parent, U.S. Pat. No. 4,990,710, each of which is relied upon and incorporated by reference herein. The catalysts in the first and second stage may be identical. For example in a cascade operation, involving two catalyst beds, the catalysts can be identical. Alternatively, the process can be undertaken over the same catalyst bed at two different temperatures.

The amount of Group VIII and Group VIA metal in the catalyst can range from 0.05 to 10 weight percent and preferably 0.1 to 5 weight percent of the microporous material. In a preferred embodiment, platinum is the Group VIII metal. However, the metal can be any Group VIII metal including those of the platinum group (platinum, iridium, and palladium), and chromium.

The modifier content of the crystalline microporous materials can range from 0.01 to 20 weight percent. Practically, the tin content will range from 0.1 to 10 weight percent.

The crystalline microporous materials of the invention can be zeolites characterized by Si/Al ratios of at least 2. However, the silica:alumina ratio of the zeolite can be up to 1000, or greater. In a preferred embodiment the aluminum content of these materials is less than 0. weight percent and more preferably less than 0.02 weight percent.

The compositions comprising Group VIA and/or Group VIII metal-containing catalysts do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the n-octane yielding more o-xylene and 2-methyl-heptane yielding mostly m-xylene, at conversions between 10 and 60%.

The crystalline microporous material has an X-ray diffraction pattern which corresponds to a zeolite, SAPO, ALPO, etc. The preferred microporous crystalline materials are crystalline in the sense that they are identifiable as isostructural with zeolites by X-ray powder diffraction pattern. Preferred zeolites are ZSM-5 and MCM-22.

In a preferred embodiment the pore size of the microporous crystalline silicates ranges from about 5 to about 8 Angstroms. In a preferred embodiment the microporous crystalline material exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein. The zeolite may alternatively be ZSM-11, ZSM-12, ZSM-23, ZSM-22, ZSM-35 and MCM-22. The microporous crystalline material can be MCM-22 which is the subject of U.S. Pat. No. 4,954,325 which is relied upon and incorporated by reference herein.

When, as in embodiments herein, the crystalline material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

The methods of synthesizing these preferred materials are described in U.S. Pat. No. 4,990,710 which is relied upon and incorporated by reference herein.

The non-acidic, crystalline, microporous, Group VIA and Group VIII metal containing materials used in the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite. When used with a matrix or binder, the catalyst of the invention will preferably be combined with non-acidic matrix or binder materials. A preferred matrix or binder material would be silica or titania.

EXAMPLES

The non-acidic catalysts included a 1.5% Pt/2.7% Sn-ZSM-5 (A), a 1.07% Pt/1.2% Sn-ZSM-5 (B), an 0.6% Pt/high silica tin-free ZSM-5 (C), a 1.6% Pt/1.1% indium-ZSM-5 (D), a 0.55% Pt/1.3% Pb-ZSM-5 (E), and a 1.07% Pt/3.2% Ga/0.2% Boron MCM-22 (F).

Reactions were conducted in down-flow 3/8" stainless steel reactors containing 1.0 g of catalyst. Where a second stage was used, 0.5 g A was placed below the reactor furnace, and heated separately. Reactor effluents were analyzed by on-line GC. Products were identified by GC-MS and by comparison of retention times with authentic samples.

n-Pentane, purity >99.4%, was introduced into the reactor by passing a stream of nitrogen through a pentane vaporizer maintained at 0° C., to provide a $N_2/C_5$ ratio of about 3. Yields are expressed in carbon weight %, based on GC areas without correction for sensitivity differences.

EXAMPLE 1

A typical product distribution observed for a tin-free Pt/ZSM-5 (C) catalyst operating at 500° C., 1.6 WHSV, 3:1 $N_2/C_5$, and atmospheric pressure, followed by a second stage Pt/Sn-ZSM-5 (A) catalyst at 210° C., is shown in Table 1 below:

TABLE 1

Product Distribution of Two-Stage Reactor
Conditions: Pt/ZSM-5, 500° C., 1.6 WHSV, 3:1 $N_2/C_5$, 210° C. 2nd Stage

| Product | Wt. % |
| --- | --- |
| Methane | 3.0 |
| Ethane | 2.6 |
| Propane | 4.0 |
| iso-Butane | 0.4 |
| n-Butane | 9.0 |
| iso-Pentane | 4.4 |
| n-Pentane | 39.3 |
| n-Pentenes | 0.2 |
| Cyclopentene | 0.3 |
| Cyclopentane | 35.0 |
| Methylcyclopentane | 0.6 |
| Benzene | 1.0 |

TABLE 1-continued

Product Distribution of Two-Stage Reactor
Conditions: Pt/ZSM-5, 500° C., 1.6 WHSV, 3:1 N₂/C₅,
210° C. 2nd Stage

| Product | Wt. % |
|---|---|
| Toluene | 0.2 |

Some products greater than C₅ were also observed: in particular, methylcyclopentane, benzene, and toluene.

The reaction temperature of the first stage was then raised to 550° C. This resulted in an increase in cyclopentane yield to 46.7%, with a selectivity of 62.4%.

EXAMPLE 2

Substitution of a tin-modified Pt/ZSM-5 catalyst (Catalyst B) for the tin-free catalyst in the first stage resulted in a significant improvement in cyclopentane selectivity. Product distributions formed over the tin-modified catalyst are shown in Table 2 below:

TABLE 2

Product Distribution over Pt/Sn-ZSM-5 (2-Stage)

| Conditions: | Temp.- | 500° C. | 550° C. | 575° C. |
|---|---|---|---|---|
| | WHSV- | 1.6 | 1.6 | 0.8 |
| | TOS(h)- | 19 | 24 | 29 |
| Product | | Wt. % | Wt. % | Wt. % |
| Methane | | 0.5 | 1.3 | 2.7 |
| Ethane | | 1.1 | 2.0 | 2.8 |
| Propane | | 1.5 | 2.6 | 3.2 |
| iso-Butane | | — | 0.2 | 0.3 |
| n-Butane | | 1.5 | 2.7 | 3.3 |
| iso-Pentane | | 3.4 | 4.1 | 3.9 |
| n-Pentane | | 55.7 | 31.1 | 22.2 |
| Cyclopentene | | 0.3 | 0.5 | 0.2 |
| Cyclopentane | | 35.5 | 54.1 | 59.7 |
| Methylcyclopentane | | 0.2 | 0.3 | 0.3 |
| Benzene | | 0.2 | 0.7 | 1.1 |
| Toluene | | — | 0.3 | 0.2 |

At 500° C., cyclopentane yields varied from 41% to 35%, with selectivities as high as 81%. At 550° C., cyclopentane yield increased to as high as 54–56%; after several hours, a 50.8% yield was obtained at 80.4% selectivity. At 575° C. and one-half the flow rate, a cyclopentane yield of 59.7% was observed, with 76.7% selectivity.

Selectivities to high octane products are even higher than the 80% cyclopentane selectivities observed, since isopentane, methylcyclopentane, benzene, and toluene can all readily be added to gasoline. Even the butane produced can be added into the gasoline, due to the reduction in RVP caused by pentane cyclization. Only $C_1$–$C_3$ have reduced value; on this basis, selectivities to high octane products approach 90–93%.

EXAMPLE 3

In a 2-stage reactor employing 1.0 g 1.6% Pt/1.1% In-ZSM-5(D) in the first stage and 0.5 g Pt/Sn-ZSM-5(A) as the second stage catalyst, n-pentane conversion to cyclopentane was observed. The N₂/C₅ ratio was approximately 3, and the second stage temperature was 220° C. At 550° C., a 48.9% yield of cyclopentane was obtained with a selectivity of 77%.

EXAMPLE 4

A 0.55% Pt/1.3% Pb-ZSM-5 (E) catalyst was used in the first stage. Under similar conditions, a 41.6% yield of cyclopentane was observed at a selectivity of 73%.

EXAMPLE 5

A low aluminum content MCM-22 zeolite was synthesized in the presence of boron and gallium. The calcined form was then treated with Pt(NH₃)₄Cl₂ in dilute NaHCO₃ solution. The exchanged zeolite was then calcined in air at 350° C. It analyzed for 1.07% Pt, 1.39% Na, 3.16% Ga, 0.20% B, and 0.073% Al.

Use of this catalyst (F) in the first stage at 500° C. resulted in a 34.7% yield of cyclopentane at a selectivity of 56%.

Thus it is apparent that there has been provided, in accordance with the invention, a process, that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is

1. A process for converting n-pentane to cyclopentane comprising contacting n-pentane with a catalyst bed in which the catalyst comprises a Group VIA or Group VIII metal and a non-acidic microporous support material
   wherein the amount of Group VIA or Group VIII metal in the catalyst ranges from 0.05 to 10 weight percent
at a temperature ranging from 300°–700° C. to form a product effluent, and passing the product effluent over a second catalyst bed maintained under a second set of conditions in which the temperature is less than 300° C.; wherein the second catalyst bed comprises a second catalyst which second catalyst comprises a Group VIA or Group VIII metal and a non-acidic microporous material
   wherein the amount of Group VIA or Group VIII metal in the catalyst ranges from 0.05 to 10 weight percent and
recovering a second product which comprises cyclopentane.

2. The process of claim 1, wherein the non-acidic support comprises a non-acidic crystalline microporous material.

3. The process of claim 1, wherein the non-acidic microporous material contains a modifier selected from the group consisting of tin, indium, gallium, lead, thallium and sulfur, wherein the modifier content of the crystalline microporous materials ranges from 0.01 to 20 weight percent.

4. The process of claim 1, wherein the material exhibits the X-ray diffraction pattern of a zeolite.

5. The process of claim 3, wherein the material exhibits the X-ray diffraction pattern of a zeolite.

6. The process of claim 4, wherein the zeolite is ZSM-5.

7. The process of claim 5, wherein the zeolite is ZSM-5.

8. The process of claim 4, wherein the zeolite is ZSM-5, ZSM-11, ZSM-12. ZSM-22, ZSM-23, ZSM-35 or MCM-22.

9. The process of claim 5, wherein the zeolite is ZSM-5, ZSM-11, ZSM-12. ZSM-22, ZSM-23, ZSM-35 or MCM-22.

10. The process of claim 5, wherein the first stage temperature ranges from 300° C. to 600° C.

11. The process of claim 10, wherein the first stage temperature ranges from 450°-600° C.

12. The process of claim 11, wherein the second stage temperature ranges from 200° to 300° C.

13. The process of claim 11, wherein the second stage temperature ranges from 25° to 250° C.

14. The process of claim 1, wherein the first and second stages are undertaken in a cascade operation without interstage processing of the first stage product effluent.

15. The process of claim 1, which further includes cofeeding an inert diluent with said n-pentane.

16. The process of claim 15, wherein said diluent is nitrogen, methane or aromatic compounds, and admixtures thereof.

17. The process of claim 16, wherein the diluent is selected from the group consisting of $C_6$-$C_8$ aromatics and admixtures thereof.

18. A process for converting a n-pentane containing feed to a cyclopentane enriched product exhibiting research octane number (RON) greater than that of the feed comprising contacting said n-pentane containing feed with a catalyst bed in which the catalyst comprises a metal selected from the group consisting of Group VIA and Group VIII metals and a non-acidic microporous material wherein the amount of metal in the catalyst ranges from 0.05 to 10 weight percent at a temperature ranging from 300°-700° C. to form a product effluent, and passing the product effluent over a second catalyst bed maintained under a second set of conditions in which the temperature is less than 300° C.; wherein the second catalyst bed comprises a second catalyst comprising Group VIA or a Group VIII metal and a non-acidic crystalline microporous material wherein the amount of metal in the catalyst ranges from 0.05 to 10 weight percent and recovering said cyclopentane enriched product.

19. The process of claim 18, wherein the material exhibits the X-ray diffraction pattern of a zeolite.

20. The process of claim 18, wherein the zeolite is ZSM-5, ZSM-11, ZSM-12, ZSM-22, ZSM-23, ZSM-35 or MCM-22.

21. The process of claim 20, wherein the zeolite is ZSM-5 or MCM-22.

22. The process of claim 21, wherein the zeolite is ZSM-5.

23. The process of claim 18, which further includes cofeeding an inert diluent with said n-pentane.

24. The process of claim 23, wherein said diluent is nitrogen, methane or aromatic compounds, and admixtures thereof.

25. The process of claim 24, wherein the diluent is selected from the group consisting of $C_6$-$C_8$ aromatics and admixtures thereof.

* * * * *